United States Patent [19]
Bruce et al.

[11] 3,963,927
[45] June 15, 1976

[54] DETECTION OF HIDDEN INSECTS

[75] Inventors: William A. Bruce; Marion W. Street, Jr., both of Savannah, Ga.

[73] Assignee: The United States of America as represented by the Secretary of Agriculture, Washington, D.C.

[22] Filed: June 18, 1975

[21] Appl. No.: 588,108

[52] U.S. Cl. ................................. 250/338; 356/51
[51] Int. Cl.² ........................................ G01N 21/34
[58] Field of Search ............... 250/343, 338; 356/51

[56] References Cited
UNITED STATES PATENTS

| | | | |
|---|---|---|---|
| 2,930,893 | 3/1960 | Carpenter et al. | 356/51 |
| 3,513,307 | 5/1970 | Dudgeon | 250/338 |
| 3,783,284 | 1/1974 | McMormack | 356/51 |
| 3,922,551 | 11/1975 | Williams | 250/343 |
| 3,925,666 | 12/1975 | Allan et al. | 250/338 |

*Primary Examiner*—Alfred E. Smith
*Assistant Examiner*—T. N. Grigsby
*Attorney, Agent, or Firm*—M. Howard Silverstein

[57] ABSTRACT

A system or method of detecting hidden insects by the measurement of $CO_2$ respired is described. The system consists of a series of valves, pressure regulator, gauges, and an infrared analyzer. After purging the system is sealed and the $CO_2$ allowed to build up. The $CO_2$ then moves through the infrared gas analyzer as a bolus and the detection is thus achieved.

10 Claims, 1 Drawing Figure

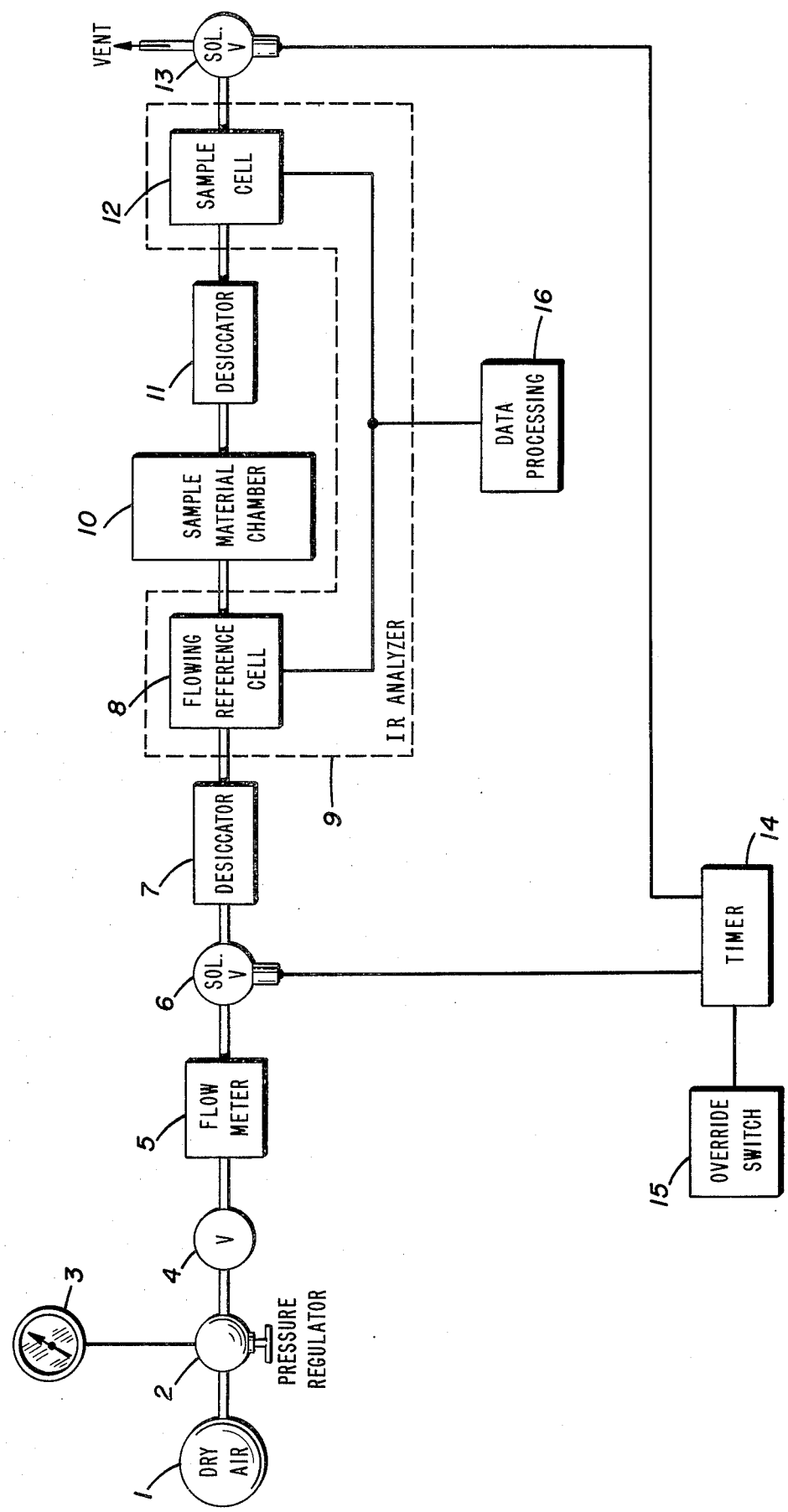

DETECTION OF HIDDEN INSECTS

PRIOR ART AND BACKGROUND OF INVENTION

Due to the destruction and damage caused by insects in the world, increased efficiency of yield and protection from these insects has made the detection of insect infestation critical. Regulatory operations, quarantine operations, and quality control in production and marketing channels requires technology for early, rapid, and foolproof insect detection. In addition these methods must be economical as well as meet the criteria of non destructive testing. Heretofore, detection of hidden infestations of insects and mites has been accomplished by various means including sound, X-rays, chemical reagents, microwaves and nuclear magnetic resonance. However, these foregoing methods are either limited to small sample size, time consuming, not foolproof, prohibitively expensive, or do not meet the requirements for nondestructive testing.

It is known that insects and mites produce carbon dioxide ($CO_2$) as a result of their respiratory and metabolic processes. However, the quantity of $CO_2$ produced by an insect per unit time is so small as to be difficult to detect in the presence of naturally present atmospheric $CO_2$. Small quantities of such insect-produced $CO_2$ would show up at best only as a slow, long-term drift in baseline under continuous flow testing and would not be suitable for rapid detection applications. Herein lies the uniqueness of the instant invention. The sample chamber is purged with carrier gas and then sealed off for an interval during which the $CO_2$ emitted by the insect(s) is allowed to build up and reach a concentration sufficient for detection. The gas flow is then set in motion so that the higher $CO_2$ concentration bolus moves through the detector cell generating a significant, time-synchronous, transient signal above the background levels of the system.

This invention uses alternating intervals of insect $CO_2$ buildup and purge by a carrier gas to produce an identifiable signal of insect presence. The carrier gas is normally dry air. Use of the invention in no way alters the test material, does not affect the insects, produces no by-products, and in no way pollutes the environment.

The invention can be arranged for use on ships railcars, motor vehicles, trailers, or aircraft; or can be placed outside or in warehouses, grainholding and handling facilities, laboratories, homes, farm areas, military or government facilities whether fixed or mobile, or commercial establishments. The equipment can be operated in either a fixed or portable manner and can be used for local or remote inspection, surveillance, or monitoring in any of these application. It can be operated manually or automatically in any of these applications.

OBJECTIVES

It is the object of this invention to provide a system or method for the detection of hidden insects. More specifically, it is the object of this invention to provide a method or system for the detection of hidden insects by use of infrared analysis of carbon dioxide. Another object of this invention is to detect hidden insects or mites by a non-destructive testing procedure. Another object of this invention is the detection of hidden insects by building up a concentration of carbon dioxide for measurement rather than measuring a continuous low concentration carbon dioxide.

Still another object of this invention is to provide an efficient and reliable nondestructive testing method or system for the detection of hidden insects at a relatively cheap cost.

DESCRIPTION OF THE INVENTION

FIG. 1 is a schematic diagram of the invention.

Referring now to the single FIG. 1, dry air 1 which is controlled by pressure regulator 2 and gauge 3 is adjusted by needle valve 4 for appropriate flow rate by observing flow meter 5. Inlet solenoid valve 6 and outlet solenoid valve 13 are controlled either by tandem recycling timer 14 or manualoverride switch 15. The manual-override switch 15 permits initial purge of the system after sample introduction. Then, system control is transferred to timer 14, which is set to alternate between sample gas collection and detection time intervals.

The system has two operational states defined as follows:

State I: Valves 6, 13, open and air flowing through the system for initial purging or sample gas detection.

State II: Valves 6 and 13, closed, no air flow, system is sealed to permit $CO_2$ concentration buildup in sample material chamber 10 during sample gas collection interval.

When valve 6 and 13 are open, air flows through desiccator 7 and through flowing reference cell 8 of IR analyzer 9, thence through sample chamber 10, through desiccator 11, through sample cell 12 of IR analyzer 9, through outlet solenoid valve 13, and is vented to the atmosphere. Desiccators 7 and 11 are appropriately placed to ensure freedom from moisture within the analyzer, and they also serve to dampen pressure transients that normally occur when the system is switched between State I and State II.

The preferred mode of operation of the IR analyzer is as a differential system. That is, the reference cell 8 is of the flowing type rather then sealed, and the difference in $CO_2$ concentration between reference cell 8 and sample cell 12 is detected. For a particular tightly-defined application a sealed reference cell 8 could be used.

It has been found that the intermittent flow method comprising initial purge after sample introduction (State I), sample gas collection interval (State II), and detection interval (State I) is essential to enhance detection capability and efficiency. Therefore, a time interval is allowed for $CO_2$ buildup. This is accomplished when valves 6 and 13 are closed, and there is no air flow through the system. The system is sealed to permit $CO_2$ concentration buildup in sample chamber 10 for a gas collection interval. The $CO_2$ buildup in the sample chamber 10 during the sample gas collection interval subsequently moves as a bolus through the sample cell 12 of infrared analyzer 9 during the detection interval where it is detected and used to actuate a display, recording, warning, control, or data processing device 16. This is accomplished by opening valves 6 and 13 simultaneously. The higher $CO_2$ concentration is pushed forward as a bolus passing through desiccator 11 and to sample cell 12 of infrared analyzer 9 where measurement of the $CO_2$ concentration is recorded, and thence out through valve 13 to the atmosphere.

The system or method as described is the preferred mode of operation. However, the system can also work using a negative pressure or suction for generating the flow (throughout) rather than using positive pressure as described.

The number of minutes that the sample of agricultural material must be retained in sealed zone of chamber 10 may be determined through routine experimentation with control samples containing known quantities of identified insects.

The term insects is understood to be arthopods of Insecta, Acari, and Aranae of any species, in any way associated with the sample material.

It has been determined that insects, such as the rice weevil and the flour beetle, found in stored agricultural products can be detected while in the commodity by using a Luft-type differential infrared $CO_2$ gas analyzer with dry air as the carrier gas at 5 psi line pressure, 2000 ml/min air flow, 0.5-liter sample chamber, a 1-min sample gas collection interval, and a 2-min detection interval, with an analyzer sensitivity of 0–50 p.p.m.

It has also been determined that the intermittent flow can be accomplished by the switching on and off of a pump utilized for the carrier gas (air) supply. This arrangement can be utilized rather than a valve controlled air source.

We claim:

1. A method for detecting hidden insects in agricultural material comprising:
    a. placing a sample of said material in a substantially enclosed zone;
    b. purging said zone with dry air;
    c. sealing said zone for a time interval to allow the buildup of $CO_2$ in said zone from hidden insects in said material therein;
    d. again purging said zone with dry air;
    e. measuring by infrared analysis the $CO_2$ content of said dry air in step (d), prior to introduction into said zone;
    f. measuring by infrared analysis the $CO_2$ content of gas which is purged from said zone in step (d);
    g. comparing the measurements in steps (e) and (f) so as to determine the amount of $CO_2$ which has been imparted to said dry air by said hidden insects in said zone;
    h. sealing said zone for the same time interval as in step (c) to again allow the buildup of $CO_2$ in said zone from said hidden insects; and
    i. thereafter repeating steps (d), (e), (f), and (g).

2. The method of claim 1 wherein said dry air is supplied to said zone at about 5 psig, and about 2000 ml/min flow; and the volume of said zone is about 0.5 liter.

3. The method of claim 1 wherein the said time interval in step (c) is about 2 minutes.

4. The method of claim 1 wherein a partial vacuum draws dry air through said zone during said method.

5. The method of claim 3 wherein a partial vacuum draws dry air through said zone during said method.

6. Apparatus for detecting hidden insects in agricultural material comprising:
    a. a substantially enclosed chamber for holding a sample of said material;
    b. first and second conduit means connected to said chamber to purge gas from said chamber;
    c. means to supply dry air to said first conduit means to purge gas from said chamber into said second conduit means;
    d. means to seal said chamber after purging thereof;
    e. infrared analysis means disposed in said first conduit means to measure the $CO_2$ content of said dry air before it enters said chamber;
    f. infrared analysis means disposed in said second conduit means to measure the $CO_2$ content of said gas which exits from said chamber during said purging; and
    g. means to compare the analyzer measurements from said first and second conduit means so as to determine the amount of $CO_2$ which has been imparted to said dry air by said hidden insects in said enclosed chamber.

7. The apparatus of claim 6 wherein said means to supply dry air to said chamber first conduit means comprises a desiccator disposed in said first conduit means.

8. The apparatus of claim 6 wherein said means to seal said chamber comprises first valve means in said first conduit means, second valve means in said second conduit; and means connected to said first and second valve means to simultaneously completely open and simultaneously completely close said first and second valve means.

9. The apparatus of claim 6 further including flow regulating means disposed in said first conduit means upstream from said first valve means.

10. The apparatus of claim 8 further including flow regulating means disposed in said first conduit means upstream from said first valve means.

* * * * *